United States Patent [19]

Sattich

[11] Patent Number: 5,304,683
[45] Date of Patent: Apr. 19, 1994

[54] CONVERSION OF ALKYL MERCAPTAN TO DIALKYL SULFIDE AND CATALYST THEREFOR

[75] Inventor: Willaim E. Sattich, Bartlesville, Okla.

[73] Assignee: Phillips Petroleum Company, Bartlesville, Okla.

[21] Appl. No.: 908,103

[22] Filed: Jul. 2, 1992

[51] Int. Cl.⁵ .......................................... C07C 319/18
[52] U.S. Cl. ........................................ 568/59; 568/60
[58] Field of Search ..................... 568/60, 59, 38, 58

[56] References Cited

U.S. PATENT DOCUMENTS

| | | | |
|---|---|---|---|
| 2,035,121 | 4/1932 | Frolich | 568/60 |
| 3,036,133 | 7/1960 | Goshorn et al. | 568/60 |
| 3,051,758 | 8/1962 | Franz et al. | 568/60 |
| 4,652,546 | 3/1987 | Aldag et al. | 502/307 |
| 4,937,385 | 6/1990 | Buchholz et al. | 568/26 |

OTHER PUBLICATIONS

Reid, *Organic Chemistry of Bivalent Sulfur*, vol. I, pp. 110–111, and 118–119, 1958.
ACS Div. Petrol. Chem. Meeting (Allison et al, Sep. 8–13, 1968).
Chem. Abstr. 72:131961y (Allison et al, 1970).
Mashkina et al, React. Kinet. Catal. Lett. 43(2):381–386, 1991.

*Primary Examiner*—Marianne M. Cintins
*Assistant Examiner*—Margaret Page
*Attorney, Agent, or Firm*—Lucas K. Shay

[57] ABSTRACT

A process for converting at least one alkyl mercaptan to a dialkyl sulfide can be carried out by contacting the alkyl mercaptan, and optionally an alkene, with an alumina catalyst under conditions sufficient to substantially covert the alkyl mercaptan to dialkyl sulfide. For example, ethyl mercaptan can by advantageously fed at a rate of about 0.5 to about 10 parts by weight per part by weight of the catalyst per hour over the catalyst at elevated temperature and pressure to produce diethyl sulfide.

14 Claims, No Drawings

CONVERSION OF ALKYL MERCAPTAN TO DIALKYL SULFIDE AND CATALYST THEREFOR

FIELD OF THE INVENTION

The present invention relates to catalytic conversion of an alkyl mercaptan to a dialkyl sulfide.

BACKGROUND OF THE INVENTION

Dialkyl sulfides are important industrial chemicals. They can be used as solvents for anhydrous mineral salts, in plating baths for coating metals with gold or silver, and as intermediates for preparing other sulfur-containing chemicals.

Although dialkyl sulfides can be produced by UV-promoted addition of alkyl mercaptans to alkenes, UV reactors may not always be available. Dialkyl sulfides can also be produced as by-products in the production of alkyl mercaptans by the reaction of alkenes and hydrogen sulfide catalyzed by an acid, a base, or supported cobalt/molybdenum, followed by separation from the mercaptans.

However, it has been found that in order to sufficiently increase dialkyl sulfide production in the alkyl mercaptan process, the hydrogen sulfide feed has to be reduced to less than one mole per mole of the alkene feed. Under such condition, a large amount of heat is generated by the reaction creating a problem for controlling the heat in a production plant.

It is therefore desirable to develop a process that utilizes alkyl mercaptans produced in the reaction of alkenes and hydrogen sulfide for the production of dialkyl sulfides. It would be a valuable contribution to the art if a process for increasing the production of the dialkyl sulfide is developed which does not require UV light or a high ratio of alkene to hydrogen sulfide.

SUMMARY OF THE INVENTION

An object of the present invention is to develop a process for converting an alkyl mercaptan to a dialkyl sulfide with a high conversion rate. Another object of the present invention is to obtain a dialkyl sulfide in high yields. A further object of the present invention is to provide an efficient catalyst for the conversion of an alkyl mercaptan to a dialkyl sulfide. One of the advantages of the present invention is that once the alkyl mercaptan, produced from an alkene and hydrogen sulfide, is converted to the dialkyl sulfide, hydrogen sulfide is released which can be used to react the alkene to further produce the alkyl mercaptan. Other objects, advantages, features and aspects will become more apparent as the invention is more fully disclosed in the following disclosure and claims.

According to the present invention, a process for converting at least one alkyl mercaptan to a dialkyl sulfide is provided which comprises contacting the alkyl mercaptan, and optionally an alkene, with a catalytic amount of an alumina catalyst under conditions sufficient to substantially convert said alkyl mercaptan.

DETAILED DESCRIPTION OF THE INVENTION

The present invention provides a process for catalytic conversion of an alkyl mercaptan to a dialkyl sulfide. Alkyl mercaptans suitable for the invention have the formula of RSH or R'SH where R and R' can be the same or different, are $C_1-C_{20}$ alkyls, and can be linear, branched, or cyclic. Examples of suitable alkyl mercaptans include, but are not limited to, methyl mercaptan, ethyl mercaptan, propyl mercaptan, isopropyl mercaptan, butyl mercaptan, isobutyl mercaptan, t-butyl mercaptan, pentyl mercaptan, isoamyl mercaptan, hexyl mercaptan, cyclohexyl mercaptan, heptyl mercaptan, octyl mercaptan, t-nonyl mercaptan, t-dodecyl mercaptan, and mixtures of any two or more thereof.

The dialkyl sulfide product of the present invention has a general formula of RSR' where R and R' can be the same or different, are $C_1-C_{20}$ alkyls, and can be linear, branched, or cyclic. Examples of suitable dialkyl sulfides include, but are not limited to, dimethyl sulfide, diethyl sulfide, methyl ethyl sulfide, dipropyl sulfide, diisopropyl sulfide, di-t-butyl sulfide, dicyclohexyl sulfide, di-t-nonyl sulfide, di-t-dodecyl sulfide, and mixtures thereof.

The catalyst of the present invention comprises an alumina. Examples of suitable alumina are alpha-alumina, gamma-alumina, a mixture of alpha alumina and gamma alumina or any mixture of any of the above-mentioned aluminas with metal oxides or metal sulfides such as, but not limited to, sodium oxide, sodium sulfide, potassium oxide, potassium sulfide, cobalt oxide, cobalt sulfide, nickel oxide, nickel sulfide, molybdenum oxide, molybdenum sulfide or any combination of any two are more thereof. The presently preferred alumina for use in the process of the present invention is a gamma alumina. The presently most preferred gamma alumina has a surface area in the range of from about 100 to about 250 $m^2/g$, a pore volume in the range of from about 0.4 to about 0.8 ml/g and a density in the range of from about 0.6 to about 0.8 g/ml.

In the conversion of alkyl mercaptan to dialkyl sulfide, hydrogen sulfide is released. The hydrogen sulfide produced can be used to react with an alkene to produce additional alkyl mercaptan. The alkene used for this reaction should have the same number of carbon atoms as the alkyl mercaptan, i.e. preferably from 1 to 20 carbon atoms, described above and can produce the alkyl mercaptan upon reacting with the hydrogen sulfide. Addition of the alkene can be done at any stage of the process. For more efficient utilization of the released hydrogen sulfide it is preferred to include the alkene in the reaction mixture with the alkyl mercaptan. Furthermore, the alkene should preferably be the one that produces the same alkyl mercaptan upon reacting with the hydrogen sulfide.

A batch or continuous process can be employed in the process of the present invention. Any continuous process such as using a fixed bed reactor can be employed. The selection of a batch or continuous process is a matter of preference of those skilled in the art. A solvent can also be employed in the process of the present invention if it facilitates the conversion.

The process of the present invention can be conducted over a wide range of temperatures and pressures that are sufficient to convert the alkyl mercaptan to the dialkyl sulfide. Generally, the reaction can be carried out at as low as about 100° C. and as high as about 1000° C. A preferred temperature range from about 200° C. to about 600° C., most preferably from 240° C. to 350° C.

Broadly, the conversion of the alkyl mercaptan can be carried out from about atmospheric pressure up to as high as about 400 atmospheres. A preferred pressure is in the range of from about 10 atmospheres to about 200 atmospheres, most preferably from 15 atmospheres to 35 atmospheres.

In a continuous process, the alkyl mercaptan is generally fed to a reactor containing the alumina catalyst at such a rate that the conversion of the alkyl mercaptan and the selectivity to the dialkyl sulfide are high. A similar feed rate is generally used for the alkene, if present, in the reaction mixture. The feed rate, when the reactants are in gaseous phase, is preferably in the range from about 0.5 to about 10 and most preferably in the range of from 0.1 to 3.0 weight hourly space velocity (parts by weight of feed per part by weight of catalyst per hour; hereinafter referred to as WHSV).

The following non-limiting examples are provided to further illustrate the practice of the present invention.

EXAMPLE I

This is a comparative example illustrating the conversion of an alkyl mercaptan (ethyl mercaptan) to dialkyl sulfide (diethyl mercaptan) catalyzed by Co/Mo on alumina.

The runs were conducted by passing ethyl mercaptan and ethylene through a 29 in. long by 11/16 in. inner diameter stainless steel tube packed with a catalyst. Ethyl mercaptan was fed using a precalibrated LAPP-30 pump and ethylene was fed using a precalibrated combination of a micrometer valve and rotometer. Pressure was controlled via a Moore valve downstream from the catalyst tube. The catalyst tube was heated with a four-zone electric furnace. The first zone heated a portion of the tube containing only glass beads and was used to preheat the feed prior to contacting the catalyst. The latter three zones heated the portion of the tube containing the catalyst. External temperatures were monitored and controlled via four thermocouples (one in the center of each zone) inserted between the inside of the heating furnace and the outside of the catalyst tube and connected to four temperature controllers which controlled the power supply to the heating furnace. Internal catalyst bed temperatures were monitored at the center of each zone via thermocouples inserted through a ¼ in. outer diameter tube in the center of the catalyst tube. The catalyst (75.3 g) described below was used.

| Engelhard HPC-60K (commercially available from Engelhard Corp.) 1/10 in. cloverleaf extrudate | |
|---|---|
| Cobalt | 5.0 wt. % |
| Molybdenum | 16.0 wt. % |
| Sodium | 0.04 wt. % |
| Sulfate | 0.1 wt. % |
| Iron | 0.03 wt. % |
| Surface Area | 210 m$^2$/g |
| Pore Volume | 0.46 mL/g |
| Density | 0.753 g/mL |

To start a run, the reactor was brought to the desired conditions and allowed to remain at those conditions for at least one hour before any sampling was done. After that time, samples of the effluent gas stream were collected, using a gas-tight syringe, from a septum port just downstream from the Moore valve. The gas samples were immediately analyzed by gas chromatography.

For analysis of ethylene, ethane, and hydrogen sulfide content, a three foot Poropak-Q column leading to a thermal conductivity detector was used (injector 250° C., detector 300° C., oven 35° C., helium flow 30 mL/min.). For analysis of ethyl mercaptan, diethyl sulfide, diethyl disulfide, and heavies content, a six foot 5% OV-101 column leading to a flame ionization detector was used (injector 250° C., detector 300° C., oven 35° C. for three minutes, ramp 15° C./min. for 14 minutes, 245° C. for three minutes, helium flow 60 mL/min.).

Calculated weight percentages of ethylene, ethane, hydrogen sulfide, ethyl mercaptan, diethyl sulfide, and diethyl disulfide, as well as ethyl mercaptan conversion, ethylene conversion, and diethyl sulfide selectivity data are tabulated in Table I.

TABLE I

Continuous Conversion of Ethyl Mercaptan to Diethyl Sulfide

| Run | Temp. °C. | Press. atm | Ethyl Mercaptan WHSV[a] | Weight Percent of Major Components (wt. %)[b] | | | | | | Ethyl Mercaptan % Conv. | Diethyl Sulfide % Sel. |
|---|---|---|---|---|---|---|---|---|---|---|---|
| | | | | Ethylene | Ethane | Hydrogen Sulfide | Ethyl Mercaptan | Diethyl Sulfide | Diethyl Disulfide | | |
| 1 | 260 | 20.4 | 4.5 | 0.5 | 1.1 | 5.9 | 78.3 | 11.2 | 1.3 | 21.7 | 70.9 |
| 2 | 260 | 20.4 | 8.9 | 0.4 | 1.2 | 7.3 | 73.6 | 14.1 | 2.2 | 26.4 | 73.8 |
| 3 | 260 | 6.8 | 4.5 | 0.4 | 0.7 | 4.5 | 83.3 | 8.2 | 1.4 | 16.7 | 67.6 |
| 4 | 260 | 20.4 | 4.5 | 0.4 | 0.9 | 5.4 | 80.9 | 10.5 | 1.4 | 19.1 | 76.7 |
| 5 | 280 | 27.2 | 6.5 | 0.8 | 1.8 | 10.9 | 60.8 | 20.7 | 3.0 | 39.2 | 73.3 |
| 6 | 280 | 27.2 | 2.8 | 0.6 | 1.9 | 12.0 | 55.9 | 24.0 | 2.4 | 44.1 | 74.7 |
| 7 | 240 | 13.6 | 2.8 | 0.1 | 0.3 | 1.8 | 93.3 | 3.6 | 0.6 | 6.7 | 73.4 |
| 8 | 240 | 27.2 | 6.5 | 0.1 | 0.6 | 2.6 | 89.0 | 4.6 | 2.0 | 11.0 | 54.7 |
| 9 | 240 | 27.2 | 2.8 | 0.1 | 0.5 | 2.5 | 90.6 | 5.0 | 0.8 | 9.4 | 73.2 |
| 10 | 280 | 13.6 | 6.5 | 1.2 | 1.7 | 14.7 | 44.3 | 29.9 | 5.8 | 55.7 | 73.0 |
| 11 | 260 | 20.4 | 4.5 | 0.4 | 0.9 | 5.6 | 77.4 | 10.7 | 3.8 | 22.5 | 63.3 |
| 12 | 220 | 20.4 | 4.5 | 0.2 | 0.9 | 5.0 | 77.9 | 8.7 | 4.1 | 22.1 | 51.1 |
| 13 | 260 | 20.4 | 1.1 | 0.5 | 1.3 | 8.5 | 68.3 | 16.9 | 2.3 | 31.7 | 73.1 |
| 14 | 260 | 20.4 | 4.5 | 0.2 | 0.5 | 3.7 | 86.8 | 7.4 | 1.1 | 13.2 | 77.5 |
| 15 | 240 | 13.6 | 6.5 | 0.2 | 0.6 | 3.3 | 84.3 | 5.4 | 3.6 | 15.7 | 43.8 |
| 16 | 280 | 13.6 | 2.8 | 1.4 | 2.0 | 13.7 | 47.2 | 25.4 | 5.9 | 52.8 | 65.1 |
| 17 | 260 | 20.4 | 4.5 | 0.5 | 1.2 | 6.0 | 78.1 | 10.5 | 2.6 | 21.9 | 66.2 |
| 18 | 260 | 34.0 | 4.5 | 1.0 | 2.8 | 11.5 | 59.4 | 18.3 | 5.2 | 40.6 | 63.0 |
| 19 | 300 | 20.4 | 4.5 | 1.3 | 2.0 | 17.1 | 35.8 | 34.9 | 3.1 | 64.2 | 74.2 |
| 20 | 220 | 27.2 | 1.1 | 0.1 | 0.3 | 2.1 | 92.4 | 4.8 | 0.2 | 7.6 | 87.6 |
| 21 | 245 | 23.8 | 2.2 | 0.3 | 0.9 | 5.3 | 80.1 | 10.2 | 2.7 | 19.9 | 69.7 |
| 22 | 225 | 23.8 | 1.1 | 0.2 | 0.6 | 4.1 | 85.2 | 8.5 | 1.1 | 14.8 | 79.8 |
| 23 | 270 | 23.8 | 2.2 | 0.9 | 1.9 | 11.0 | 60.0 | 20.1 | 4.5 | 39.9 | 69.5 |

[a]Weight Hourly Space Velocity in g/g catalyst/hr
[b]Remainder is unidentified heavies Table I shows that, using Co/Mo on alumina as catalyst, the conversion of ethyl mercaptan ranged from 6.7% (run 7) at 240° C., under 13.6 atmospheres, and with a feed rate of 2.8 g mercaptan per g catalyst per hour to 64.2% (run 19) at 300° C., under 20.6 atmospheres, and with a feed rate of 4.5 g mercaptan per g catalyst per hour. Table I also shows that the selectivity to diethyl sulfide is generally less than 80% with the exception of run 20 which had a selectivity of 87.6%. However, run 20 also shows a very low conversion. It is concluded, from the results of Table I which represent a variety of variation of operating parameters, that both high conversion and selectivity cannot be obtained at the same time by using Co/Mo supported on alumina as catalyst.

The results in Table I further show that undesirable by-products, mainly ethylene and ethane, were present in the product mixture in amounts as high as 3.8 wt. % (run 18).

EXAMPLE II

This example illustrates the inventive process using a gamma alumina as catalyst to catalyze the conversion of ethyl mercaptan to diethyl sulfide.

The runs were carried out the same as those described in Example I except that, instead of Co/Mo supported on alumina, 66.8 g of the gamma alumina catalyst described below was used.

| Gamma alumina CONDDEA 19.132/88 (1–3 mm spheres, commercially available from CONDEA CHEMIE) | |
|---|---|
| Surface area | 136 m²/g |
| Pore Volume | 0.49 ml/g |
| Density | 0.668 g/ml |

The results are shown in Table II.

EXAMPLE III

This example shows that addition of ethylene to a reaction mixture of the inventive process greatly improves the selectivity to diethyl sulfide while maintaining the conversion at about 60%.

The runs were carried out as those described in Example II except that ethylene was fed, at a rate shown in Table III, to the reactor. The results are shown in Table III.

TABLE III

Continuous Conversion of Ethyl Mercaptan to Diethyl Sulfide in the Presence of Ethylene

| Run | Temp. °C. | Press. atm | Ethyl Mercaptan WHSV[a] | Ethylene WHSV[a] | Ethylene | Ethane | Hydrogen Sulfide | Ethyl Mercaptan | Diethyl Sulfide | Diethyl Disulfide | Ethyl Mercaptan % Conv. | Diethyl Sulfide % Sel. | Ethylene % Conv. |
|---|---|---|---|---|---|---|---|---|---|---|---|---|---|
| 26 | 245 | 23.8 | 2.4 | 0.1 | 4.4 | <0.1 | 5.7 | 41.5 | 46.7 | 1.0 | 56.5 | 96.5 | 5 |
| 27 | 270 | 23.8 | 2.4 | 0.1 | 3.2 | <0.1 | 7.1 | 34.1 | 54.3 | 0.6 | 64.3 | 97.8 | 30 |
| 28 | 270 | 23.8 | 2.3 | 0.2 | 4.7 | <0.1 | 5.5 | 28.0 | 61.3 | 0.3 | 69.2 | 99.2 | 50 |
| 29 | 245 | 23.8 | 2.3 | 0.2 | 3.9 | <0.1 | 3.4 | 39.8 | 52.3 | 0.4 | 56.2 | 98.8 | 55 |

Weight Percent of Major Components (wt. %)[b]

[a]Weight Hourly Space Velocity in g/g catalyst/hr
[b]Remainder is unidentified heavies Table III shows that the selectivity increased to as high as 99.2% (run 28) from 90.8% (run 25) under same temperatures and pressures. The conversion of ethyl mercaptan also increased from 61.4% (run 25) to 69.2% (run 28). The production of hydrogen sulfide was also decreased from 15.9 wt. % (run 25) to 5.5 wt. % (run 28). The results in Table III demonstrate that addition of ethylene improved the conversion of ethyl mercaptan to diethyl sulfide and reduced the hydrogen sulfide in the product mixture. It is not surprising that the product mixture also contained some unreacted ethylene. However, the excess unreacted ethylene can be reduced by refining the process.

EXAMPLE IV

This is a comparative example illustrating that, using Co/Mo on alumina, addition of ethylene does not improve the ethyl mercaptan conversion and diethyl sulfide selectivity as shown in the inventive Example III.

The runs were carried out the same as those described in Example III except that the catalyst Co/Mo on alumina described in Example I was used. The results shown in Table IV indicate that under the same

TABLE II

Continuous Conversion of Ethyl Mercaptan to Diethyl Sulfide Catalyzed by Gamma Alumina

| Run | Temp. °C. | Press. atm | Ethyl Mercaptan WHSV[a] | Ethylene | Ethane | Hydrogen Sulfide | Ethyl Mercaptan | Diethyl Sulfide | Diethyl Disulfide | Ethyl Mercaptan % Conv. | Diethyl Sulfide % Sel. |
|---|---|---|---|---|---|---|---|---|---|---|---|
| 24 | 220 | 27.2 | 1.3 | <0.1 | <0.1 | 2.6 | 88.1 | 7.0 | 1.5 | 11.9 | 76.0 |
| 25 | 270 | 23.8 | 2.5 | <0.1 | <0.1 | 15.9 | 38.6 | 41.3 | 1.3 | 61.4 | 90.8 |

Weight Percent of Major Components (wt. %)[b]

[a]Weight Hourly Space Velocity in g/g catalyst/hr
[b]Remainder is unidentified heavies Table II shows that under same temperatures and pressures (for example, comparing runs 23 and 25), the inventive process using a gamma alumina as catalyst had higher conversion and selectivity than the process using Co/Mo on alumina as catalyst. Additionally, using a gamma alumina as catalyst produced little ethylene and ethane by-products (Table II, runs 24–25).

operating temperatures and pressures, the highest conversion of ethyl mercaptan was only 51.3% (run 33) and the diethyl sulfide selectivity was less than 39% on all runs. Additionally, similar to the results in Table I, Table IV also shows the production of undesirable by-product, ethane.

TABLE IV

Continuous Conversion of Ethyl Mercaptan to Diethyl Sulfide in the Presence of Ethylene

| Run | Temp. °C. | Press. atm | Ethyl Mercaptan WHSV[a] | Ethylene WHSV[a] | Weight Percent of Major Components (wt. %)[b] | | | | | | Ethyl Mercaptan % Conv. | Diethyl Sulfide % Sel. | Ethylene % Conv. |
| --- | --- | --- | --- | --- | --- | --- | --- | --- | --- | --- | --- | --- | --- |
| | | | | | Ethylene | Ethane | Hydrogen Sulfide | Ethyl Mercaptan | Diethyl Sulfide | Diethyl Disulfide | | | |
| 30 | 245 | 23.8 | 2.0 | 0.2 | 6.2 | 0.4 | 1.7 | 49.5 | 15.0 | 18.2 | 45.5 | 35.2 | 30 |
| 31 | 245 | 23.8 | 2.1 | 0.1 | 1.8 | 0.2 | 0.8 | 67.2 | 11.5 | 10.5 | 29.6 | 38.2 | 60 |
| 32 | 270 | 23.8 | 2.1 | 0.1 | 1.1 | 0.4 | 1.9 | 55.9 | 15.6 | 15.2 | 41.4 | 38.0 | 75 |
| 33 | 270 | 23.8 | 2.0 | 0.2 | 5.8 | 0.8 | 3.0 | 44.2 | 18.0 | 16.2 | 51.3 | 38.4 | 35 |

[a] Weight Hourly Space Velocity in g/g catalyst/hr
[b] Remainder is unidentified heavies The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed is:

1. A process for converting an alkyl mercaptan to a dialkyl sulfide comprising contacting said alkyl mercaptan with a catalyst, in the presence of an alkene, wherein said alkyl mercaptan has 1 to 20 carbon atoms; said catalyst consists essentially of a gamma-alumina; said alkene has 1 to 20 carbon atoms; and said process is carried out at a temperature in the range of from about 200° C. to about 600° C., at a feed rate in the range of from about 0.5 to about 10 g of said alkyl mercaptan per g of said catalyst per hour, and under a pressure of from about 10 atmospheres to about 200 atmospheres.

2. A process according to claim 1 wherein the alkyl group of said alkyl mercaptan is selected from the group consisting of linear alkyl group, branched alkyl group, cyclic alkyl group, and combinations thereof.

3. A process according to claim 2 wherein said alkyl mercaptan is ethyl mercaptan.

4. A process according to claim 1 wherein said alkene is ethylene.

5. A process according to claim 1 wherein said dialkyl sulfide has a general formula of RSR'; wherein each R and R' can be the same or different alkyl group having 1 to 20 carbon atoms.

6. A process according to claim 5 wherein said dialkyl sulfide is diethyl sulfide.

7. A process according to claim 1 wherein said temperature is in the range of from 240° C. to 350° C.

8. A process according to claim 1 wherein said feed rate is in the range of from 1.0 to 3.0 g of said alkyl mercaptan per g of said catalyst per hour.

9. A process according to claim 1 wherein said pressure is in the range of from 15 atmospheres to 35 atmospheres.

10. A process according to claim 1 wherein said feed rate is in the range of from 1.0 to 3.0 g of said alkyl mercaptan per g of said gamma-alumina per hour, said temperature is in the range of from 240° C. to 350° C., said pressure is in the range of from 15 atmospheres to 35 atmospheres; said alkyl mercaptan has a general formula of RSH or R'SH, said dialkyl sulfide has a general formula of RSR', and each R and R' can be the same or different alkyl group having 1 to 20 carbon atoms.

11. A process for converting ethyl mercaptan to diethyl sulfide comprising contacting said ethyl mercaptan with a catalyst consisting essentially of gamma alumina, in the presence of ethylene, at a temperature in the range of from 240° C. to 350° C., and under a pressure in the range of from 15 atmospheres to 35 atmospheres.

12. A process for converting an alkyl mercaptan to a dialkyl sulfide comprising contacting said alkyl mercaptan with a catalyst, in the presence of an alkene, wherein said catalyst consists essentially of a gamma-alumina and a metal compound selected from the group consisting of sodium oxide, sodium sulfide, potassium oxide, potassium sulfide, cobalt oxide, cobalt sulfide, nickel oxide, nickel sulfide, molybdenum oxide, molybdenum sulfide, and combinations of any two or more thereof; said alkyl mercaptan has 1 to 20 carbon atoms; said alkene has 1 to 20 carbon atoms; and said process is carried out at a temperature in the range of from about 200° C. to about 600° C., at a feed rate in the range of from about 0.5 to about 10 g of said alkyl mercaptan per g of said catalyst per hour, and under a pressure of from about 10 atmospheres to about 200 atmospheres.

13. A process according to claim 12 wherein said alkyl mercaptan is ethyl mercaptan.

14. A process according to claim 12 wherein said alkene is ethylene.

* * * * *